(12) United States Patent
Kern et al.

(10) Patent No.: US 7,041,442 B1
(45) Date of Patent: May 9, 2006

(54) PEPTIDES FOR VACCINATING AGAINST HUMAN CMV

(76) Inventors: Florian Kern, Wolliner Strasse 9, D-10435 Berlin (DE); Hans-Dieter Volk, Rathausstrasse 11, D-10178 Berlin (DE); Petra Reinke, Rathausstrasse 11, D-10178 Berlin (DE); Nicole Faulhaber, Fasanenstrasse 15, D-47509 Rheurdt (DE); Ingolf-Pascal Surel, Marie-Curie-Alle 16, D-10315 Berlin (DE); Elham Khatamzas, Christburger Strasse 41, D-10405 Berlin (DE)

(*) Notice: Subject to any disclaimer, the term of this patent is extended or adjusted under 35 U.S.C. 154(b) by 45 days.

(21) Appl. No.: 09/980,058

(22) PCT Filed: Jun. 2, 2000

(86) PCT No.: PCT/DE00/01854

§ 371 (c)(1),
(2), (4) Date: Apr. 10, 2002

(87) PCT Pub. No.: WO00/75180

PCT Pub. Date: Dec. 14, 2000

(30) Foreign Application Priority Data

Jun. 4, 1999 (DE) .................................. 199 27 039
Sep. 7, 1999 (DE) .................................. 199 43 702

(51) Int. Cl.
*C12Q 1/70* (2006.01)
*G01N 33/567* (2006.01)
*C07K 4/02* (2006.01)
*C12N 15/38* (2006.01)

(52) U.S. Cl. ............... 435/5; 435/7.24; 435/320.1; 530/326; 530/327; 530/328; 536/23.72

(58) Field of Classification Search ............... 530/327, 530/328, 350, 326; 514/14, 15, 44, 186.1; 424/186.1; 435/5, 7.24, 320.1; 536/23.72, 536/23.4
See application file for complete search history.

(56) References Cited

OTHER PUBLICATIONS

Belz et al (PNAS 95:13812-13817, 1998).*
Gonczol et al (Expert Opinion on Biological Therapy, 1:401-412, 2001).*
Gautier et al (European Journal of Immunology 26:1110-1117, 1996).*
Alp et al (Journal of Virology 65:4812-4820, 1991).*
Berencsi et al (Vaccine 14:369-374, 1996).*
He et al (Journal of General Virology 76:1603-10, 1995).*

* cited by examiner

*Primary Examiner*—Mary E. Mosher
(74) *Attorney, Agent, or Firm*—Norris McLaughlin & Marcus, P.A.

(57) ABSTRACT

The present invention relates to peptides or peptide derivatives of the 65 kD lower matrix phoshpoprotein of human cytomegalovirus. The peptides disclosed are useful for determining whether subjects have been exposed to human cytomegalovirus. Methods for using these peptides or derivatives thereof to determine the peptide-induced production of interferon-γ and/or TNF-α in $CD8^+$ T cells isolated from subjects are also disclosed.

8 Claims, No Drawings

SEQUENCE LISTING

<160> NUMBER OF SEQ ID NOS: 33

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 1

Gln Thr Met Leu Arg Lys Glu Val Asn Ser Gln Leu Ser Leu Gly
 1               5                  10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 2

Ala Arg Ala Lys Lys Asp Glu Leu Arg Arg Lys Met Met Tyr Met
 1               5                  10                  15

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 3

Asp Glu Leu Arg Arg Lys Met Met Tyr Met
 1               5                  10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 4

Glu Leu Arg Arg Lys Met Met Tyr Met Cys Tyr Arg Asn Ile Glu
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 5

Glu Phe Cys Arg Val Leu Cys Cys Tyr Val Leu Glu Glu Thr Ser
 1               5                  10                  15

<210> SEQ ID NO 6
<211> LENGTH: 9
<212> TYPE: PRT
<213> ORGANISM: Artificial Sequence

```
<220> FEATURE:
<223> OTHER INFORMATION: Description of Artificial Sequence: Vaccine
      against HCMV

<400> SEQUENCE: 6

Cys Arg Val Leu Cys Cys Tyr Val Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 7

Arg Val Leu Cys Cys Tyr Val Leu Glu
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 8

Val Leu Cys Cys Tyr Val Leu Glu Glu
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 9

Glu Leu Arg Arg Lys Met Met Tyr Met
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 10

Asp Glu Leu Arg Arg Lys Met Met Tyr
1               5

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 11

Cys Asn Glu Asn Pro Glu Lys Asp Val Leu Ala Glu Leu Val Lys
1               5                   10                  15
```

```
<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 12

Leu Val Lys Gln Ile Lys Val Arg Val Asp Met Val Arg His Arg
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 13

Ala Ala Asn Lys Leu Gly Gly Ala Leu Gln Ala Lys Ala Arg Ala
 1               5                  10                  15

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 14

Asp Glu Leu Arg Arg Lys Met Met Tyr Met
 1               5                  10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 15

Val Thr Ser Asp Ala Cys Met Met Thr Met Tyr Gly Gly Ile Ser
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 16

Met Ser Ile Tyr Val Tyr Ala Leu Pro Leu Lys Met Leu Asn Ile
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV
```

-continued

```
<400> SEQUENCE: 17

Val Tyr Ala Leu Pro Leu Lys Met Leu Asn Ile Pro Ser Ile Asn
1               5                   10                  15

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 18

Ala Leu Pro Leu Lys Met Leu Asn Ile
1               5

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 19

His Ile Met Leu Asp Val Ala Phe Thr Ser His Glu His Phe Gly
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 20

Asp Val Ala Phe Thr Ser His Glu His Phe Gly Leu Leu Cys Pro
1               5                   10                  15

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 21

Val Ala Phe Thr Ser His Glu His Phe
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 22

Ala Phe Thr Ser His Glu His Phe Gly
1               5
```

```
<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 23

Ala Asn Asp Ile Tyr Arg Ile Phe Ala Glu Leu Glu Gly Val Trp
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 24

Val Cys Ser Met Glu Asn Thr Arg Ala Thr Lys Met Gln Val Ile
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 25

Glu Asn Thr Arg Ala Thr Lys Met Gln Val Ile Gly Asp Gln Tyr
1               5                   10                  15

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 26

Asn Thr Arg Ala Thr Lys Met Gln Val
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 27

Thr Arg Ala Thr Lys Met Gln Val Ile
1               5

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV
```

-continued

```
<400> SEQUENCE: 28

Gln Pro Phe Met Arg Pro His Glu Arg Asn Gly Phe Thr Val Leu
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 29

Pro Leu Lys Met Leu Asn Ile Pro Ser Ile Asn Val His His Tyr
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 30

Leu Asn Ile Pro Ser Ile Asn Val His His Tyr Pro Ser Ala Ala
 1               5                  10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 31

Glu Asp Val Pro Ser Glu Lys Leu Phe Met His Val Thr Leu Gly
 1               5                  10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 32

Asp Glu Glu Glu Ala Ile Val Ala Tyr Tyr Leu Ala Thr Ala Gly
 1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Vaccine
      against HCMV

<400> SEQUENCE: 33

Glu Asn Ser Asp Gln Glu Glu Ser Glu Gln Ser Asp Glu Glu Glu
 1               5                  10                  15
```

PEPTIDES FOR VACCINATING AGAINST HUMAN CMV

The present invention relates to peptides or peptide derivatives which are useful for vaccination against human cytomegalovirus (HCMV) or for diagnoses in patients, where it can be examined whether such patients are building or have built an immune response against HCMV.

The human cytomegaloviruses (HCMV) are a group of related viruses which belong to the herpes viruses (Lutz Schneider, 1990, Pharmazie, Vol. 135, No. 27, 2396–2400). After a primary infection, the viruses remain in the body in a latent state. Physical or psychic stress can cause reactivation of latent HCMV. The virus is ubiquitous. The contamination rate of the population is around 65% in Central Europe. The cell-mediated immune response plays an essential role in the control and defense against the HCMV infection. When HCMV-specific CD8$^+$ T cells were transferred from a donor to a patient suffering from HCMV, an immune response against the HCMV infection could be observed (P. D. Greenberg et al., 1991, Development of a treatment regimen for human cytomegalovirus (CMV) infection in bone marrow transplantation recipients by adoptive transfer of donor-derived CMV-specific T cell clones expanded in vitro. Ann. N.Y. Acad. Sci., Vol.: 636, pp 184–195). Unfortunately, only few epitopes of HCMV are known which are specifically recognized by CD8$^+$ T cells. It is assumed that the immune response is essentially dominated by the 55 kD immediate-early protein 1 (IE-1) and the 65 kD lower matrix phosphoprotein (pp65) (N. J. Alp et al., 1991, Fine specificity of cellular immune responses in humans to human cytomegalovirus immediate-early 1 protein, J. Virol., Vol: 65, pp 4812–4820; and E. H. McLaughlin—Taylor et al., 1994, Identification of the major late human cytomegalovirus matrix protein pp65 as a target antigen for CD8$^+$ virus-specific cytotoxic T lymphocytes, J. Med. Virol., Vol.: 43, pp 103–110; and further, M. Wills et al., 1996, The human cytotoxic T-lymphocyte (CTL) response to cytomegalovirus is dominated by structural protein pp65: frequency, specificity, and T-cell receptor usage of pp65-specific CTL, J. Virol. 1996, Vol. 70, pp 7569–79).

In adults having a functional immune system, the infection has an uneventful course, at most showing non-specific symptoms, such as exhaustion and slightly increased body temperature. In immunodeficient adults, pulmonary diseases and retinitis are prevailing after HCMV infections. In AIDS patients, CMV infections are the cause of numerous deaths.

Various substances are employed for treatment against cytomegalovirus. For example, Foscarnet is an antiviral substance which exhibits selective activity, as established in cell cultures, against human herpes viruses, such as herpes simplex, varicella zoster, Epstein-Barr and cytomegaloviruses, as well as hepatitis viruses. The antiviral activity is based on the inhibition of viral enzymes, such as DNA polymerases and reverse transcriptases. On cytomegaloviruses, Foscarnet has a virostatic effect, but the viruses cannot be eliminated (Lutz Schneider, 1991, Neue Arzneistoffe, Vol 136, No. 46). Another problem encountered in cytomegalovirus infections is the necessity of a permanent, sometimes life-long, treatment of the patients (especially in AIDS). A further disadvantage is the fact that the cytomegaloviruses have become more resistant against the usually employed antiviral substances in recent years (e.g., Stanat et al., 1991, Antimicrob. Agents, Chemother. Vol 35, No. 11: 2191–2197 and Knox et al., 1991, Lancet, Vol 337: 1292–1293).

The sequence of 55 kD immediate-early protein 1 (IE-1) is described and defined in A. Akrigg, G. W. G. Wilkinson, J. D. Oram (1985), The structure of the major immediate early gene of human cytomegalovirus strain AD169, Virus Res., 2:107–121. The sequence of 55 kD immediate-early protein 1 has been deposited in the Swiss-Prot Data Base, European Bioinformatics Institute, under the number P13202 (=primary accession number). The 65 kD lower matrix phosphoprotein (pp65) is described in B. Rueger, S. Klages, B. Walla et al. (1987), Primary structure and transcription of the genes coding for the two virion phosphoproteins pp65 and pp71 of human cytomegalovirus, J. Virol. 61:446– 453. The sequence of 65 kD lower matrix phosphoprotein has been deposited in the Swiss-Prot Data Base, European Bioinformatics Institute, under the number PO6725 (=primary accession number). The sequences of both proteins are described in M. S. Chee, A. T. Bankier, S. Becks et al. (1990), Analysis of the protein-coding content of the sequence of human cytomegalovirus strain AD169, Curr. Top. Mircrobiol. Immunol. 154:125–169.

It has been the object of the invention to provide peptides or derivatives thereof which induce the production of interferon-γ or tumor necrosis factor α (TNF-α) in CD8$^+$ T cells, especially from subjects immunized with HCMV and having the appropriate HLA type. These peptides and their derivatives are suitable as agents for vaccination. Also, they are suitable for diagnoses to be able to establish whether a cellular immune response directed against HCMV exists in a subject, and to quantify it.

This object is achieved by peptides or peptide derivatives thereof selected from the following group of sequences:

$R_N$-Gin Thr Met Leu Arg Lys Glu Val Asn Ser Gin Leu Ser Leu Gly-$R_C$ (SEQ ID No. 1)

$R_N$-Cys Asn Glu Asn Pro Glu Lys Asp Val Leu Ala Glu Leu Val Lys-$R_C$ (SEQ ID No. 2)

$R_N$-Leu Val Lys Gin Ile Lys Val Arg Val Asp Met Val Arg His Arg-$R_C$ (SEQ ID No. 12)

$R_N$-Ala Ala Asn Lys Leu Gly Gly Ala Leu Gin Ala Lys Ala Arg Ala-$R_C$ (SEQ ID No. 13)

$R_N$-Ala Arg Ala Lys Lys Asp Glu Leu Arg Arg Lys Met Met Tyr Met-$R_C$ (SEQ ID No. 2)

$R_N$-Asp Glu Leu Arg Arg Lys Met Met Tyr Met-$R_C$ (SEQ ID No. 3)

$R_N$-Glu Leu Arg Arg Lys Met Met Tyr Met Cys Tyr Arg Asn Ile Glu-$R_C$ (SEQ ID No. 4)

$R_N$-Val- Thr Ser Asp Ala Cys Met Met Thr Met Tyr Gly Gly Ile Ser-$R_C$ (SEQ ID No. 15)

$R_N$-Glu Phe Cys Arg Val Leu Cys Cys Tyr Val Leu Glu Glu Thr Ser-$R_C$ (SEQ ID No. 5)

$R_N$-Met Ser Ile Tyr Val Tyr Ala Leu Pro Leu Lys Met Leu Asn Ile-$R_C$ (SEQ ID No. 16)

$R_N$-Val Tyr Ala Leu Pro Leu Lys Met Leu Asn Ile Pro Ser Ile Asn-$R_C$(SEQ ID No. 17)

$R_N$-Ala Leu Pro Leu Lys Met Leu Asn Ile-$R_C$ (SEQ ID No. 18)

$R_N$-His Ile Met Leu Asp Val Ala Phe Thr Ser His Glu His Phe Gly-$R_C$ (SEQ ID No. 19)

$R_N$-Asp Val Ala Phe Thr Ser His Glu His Phe Gly Leu Leu Cys Pro-$R_C$ (SEQ ID No. 20)

$R_N$-Val Ala Phe Thr Ser His Glu His Phe-$R_C$ (SEQ ID No. 21)

$R_N$-Ala Phe Thr Ser His Glu His Phe Gly-$R_C$ (SEQ ID No. 22)

$R_N$-Ala Asn Asp Ile Tyr Arg Ile Phe Ala Glu Leu Glu Gly Val Trp-$R_C$ (SEQ ID No. 23)

$R_N$-Val Cys Ser Met Glu Asn Thr Arg Ala Thr Lys Met Gin Val Ile-$R_C$ (SEQ ID No. 24)

R$_N$-Glu Asn Thr Arg Ala Thr Lys Met Gin Val Ile Gly Asp Gin Tyr-R$_C$ (SEQ ID No. 25)
R$_N$-Asn Thr Arg Ala Thr Lys Met Gin Val-R$_C$ (SEQ ID No. 26)
R$_N$-Thr Arg Ala Thr Lys Met Gln Val Ile-R$_C$ (SEQ ID No. 27)
R$_N$-Gin Pro Phe Met Arg Pro His Glu Arg Asn Gly Phe Thr Val Leu-R$_C$ (SEQ ID No. 28)
R$_N$-Pro Leu Lys Met Leu Asn Ile Pro Ser Ile Asn Val His His Tyr-R$_C$ (SEQ ID No. 29)
R$_N$-Leu Asn Ile Pro Ser Ile Asn Val His His Tyr Pro Ser Ala Ala-R$_C$ (SEQ ID No. 30)
R$_N$-Glu Asp Val Pro Ser Glu Lys Leu Phe Met His Val Thr Leu Gly-R$_C$ (SEQ ID No. 31)
R$_N$-Cys Arg Val Leu Cys Cys Tyr Val Leu-R$_C$ (SEQ ID No. 6)
R$_N$-Arg Val Leu Cys Cys Tyr Val Leu Glu-R$_C$ (SEQ ID No. 7)
R$_N$-Val Leu Cys Cys Tyr Val Leu Glu Glu-R$_C$ (SEQ ID No. 8)
R$_N$-Glu Leu Arg Arg Lys Met Met Tyr Met-R$_C$ (SEQ ID No. 9)
R$_N$-Asp Glu Leu Arg Arg Lys Met Met Tyr-R$_C$ (SEQ ID No. 10)
R$_N$-Asp Glu Lou Arg Arg Lys Met Met Tyr Met-R$_C$ (SEQ ID No. 14)
R$_N$-Asp Glu Glu Glu Ala Ile Val Ala Tyr Tyr Leu Ala Thr Ala Gly-R$_C$ (SEQ ID No. 32) or
R$_N$-Glu Asn Ser Asp Gin Glu Glu Ser Glu Gin Ser Asp Glu Glu Glu-R$_C$ (SEQ ID No. 33)

wherein
R$_N$ represents —H or an amino protective group, or at least one further amino acid outside the peptide or peptide derivative;
R$_C$ represents —OH or a carboxy protective group, or at least one further amino acid outside the peptide or peptide derivative;
wherein said pepticle derivatives have a deletion, insertion or substitution of one, two or three amino acids of the above mentioned sequences, or the sequence is truncated to nine contiguous amino acids, the deletion being an N-terminal and/or C-terminal deletion;
wherein said peptide derivatives essentially have the functionality of one of the explicitly stated peptides:
Cys Arg Val Leu Cys Cys Tyr Val Leu (SEQ ID No. 6)
Arg Val Leu Cys Cys Tyr Val Leu Glu (SEQ ID No. 7)
Val Leu Cys Cys Tyr Val Leu Glu Glu (SEQ ID No. 8)
Glu Leu Arg Ary Lys Met Met Tyr Met (SEQ ID No. 9)
Asp Glu Leu Arg Arg Lys Met Met Tyr (SEQ ID No. 10)
Asp Glu Leu Arg Arg Lys Met Met Tyr Met (SEQ ID No. 14)
Gin Thr Met Leu Arg Lys Glu Val Asn Ser Gln Leu Ser Leu Gly (SEQ ID No. 1)
Cys Asn Glu Asn Pro Glu Lys Asp Val Leu Ala Glu Leu Val Lys (SEQ ID No. 11)
Leu Val Lys Gln Ile Lys Val Arg Val Asp Met Val Arg His Arg (SEQ ID No. 12)
Ala Ala Asn Lys Leu Gly Gly Ala Leu Gln Ala Lys Ala Arg Ala (SEQ ID No. 13)
Ala Arg Ala Lys Lys Asp Glu Leu Arg Arg Lys Met Met Tyr Met (SEQ ID No. 2)
Asp Glu Leu Arg Arg Lys Met Met Tyr Met (SEQ ID No. 3)
Glu Leu Arg Arg Lys Met Met Tyr Met Cys Tyr Arg Asn Ile Glu (SEQ ID No. 4)
Val Thr Ser Asp Ala Cys Met Met Thr Met Tyr Gly Gly Ile Ser (SEQ ID No. 15)
Glu Phe Cys Arg Val Leu Cys Cys Tyr Val Leu Glu Glu Thr Ser (SEQ ID No. 5)
Met Ser Ile Tyr Val Tyr Ala Leu Pro Leu Lys Met Leu Asn Ile (SEQ ID No. 16)
Val Tyr Ala Leu Pro Leu Lys Met Leu Asn Ile Pro Ser Ile Asn (SEQ ID No. 17)
Ala Leu Pro Leu Lys Met Leu Asn Ile (SEQ ID No. 18)
His Ile Met Leu Asp Val Ala Phe Thr Ser His Glu His Phe Gly (SEQ ID No. 19)
Asp Val Ala Phe Thr Ser His Glu His Phe Gly Leu Leu Cys Pro (SEQ ID No. 20)
Val Ala Phe Thr Ser His Glu His Phe (SEQ ID No. 21)
Ala Phe Thr Ser His Glu His Phe Gly (SEQ ID No. 22)
Ala Asn Asp Ile Tyr Arg Ile Phe Ala Glu Leu Glu Gly Val Trp (SEQ ID No. 23)
Val Cys Ser Met Glu Asn Thr Arg Ala Thr Lys Met Gin Val Ile (SEQ ID No. 24)
Glu Asn Thr Arg Ala Thr Lys Met Gin Val Ile Gly Asp Gin Tyr (SEQ ID No. 25)
Asn Thr Arg Ala Thr Lys Met Gin Val (SEQ ID No. 26)
Thr Arg Ala Thr Lys Met Gin Val Ile (SEQ ID No. 27)
Gin Pro Phe Met Arg Pro His Glu Arg Asn Gly Phe Thr Val Leu (SEQ ID No. 28)
Pro Leu Lys Met Leu Asn Ile Pro Ser Ile Asn Val His His Tyr (SEQ ID No. 29)
Leu Asn Ile Pro Ser Ile Asn Val His His Tyr Pro Ser Ala Ala (SEQ ID No. 30)
Glu Asp Val Pro Ser Glu Lys Leu Phe Met His Val Thr Leu Gly (SEQ ID No. 31)
Asp Glu Glu Glu Ada Ile Val Ala Tyr Tyr Leu Ala Thr Ala Gly (SEQ ID No. 32) or
Glu Asn Ser Asp Gin Glu Glu Ser Glu Gin Ser Asp Glu Glu Glu (SEQ ID No. 32) (each of the above: sequences=reference sequence);

i.e., to induce the production of interferon-γ or TNF-α in CD8$^+$ T cells, especially from subjects immunized with HCMV and having the appropriate HLA type.

An appropriate HLA (human leukocyte antigen) type is a combination of MHC (major histocompatibility complex) class I molecules one or more of which enable the presentation of the peptides described. Only when an appropriate HLA type is present, a particular peptide can be presented, and only in this case, stimulation can occur. The following is a suitable reference for MHC as such and the antigen recognition of T cells: Abdul K. Abbas, Cellular and Molecular Immunology/A. K. Abbas, A. H. Lichtman, J. S. Prober, Chapters 5 and 6, 1991, W.B. Saunders, Philadelphia, ISBN 0-7216-3032-4.

Many patients which may be capable of vaccination have already been infected. Thus, in these patients, there will be enhancement of the immune response ("boosting"). The infection may be latent or actively manifest. Subjects having a latent virus are also to be considered "infected".

Preferred reference sequences are:
Val Cys Ser Met Glu Asn Thr Arg Ala Thr Lys Met Gln Val Ile; (SEQ ID No. 24)
Asn Thr Arg Ala Thr Lys Met Gin Val; (SEQ ID No. 26)
Glu Phe Cys Arg Val Leu Cys Cys Tyr Val Leu Glu Glu Thr Ser; (SEQ ID No. 5)
Cys Arg Val Leu Cys Cys Tyr Val Leu. (SEQ ID No. 6).

The individual amino acids have different preferences in the respective positions.

The comparison between the different amino acids is effected by exchanging an amino acid in a defined position while the other amino acids in the remaining positions are maintained. Generally, multiple substitutions are also possible.

The functions of the peptides or peptide derivatives are substantially changed when substituents are selected which are less conservative in substitution as compared to the amino acids mentioned in the following. Thus, the substituents Gly and Ser are similar to the amino acid Ala, and the substituent Lys is similar to the amino acid Arg. The substituents Gln and His are similar to the amino acid Asn; the substituent Glu is similar to the amino acid Asp; the substituent Ser is similar to the amino acid Cys; the substituent Asn is similar to the amino acid Gln; the substituent Asp is similar to the amino acid Glu; the substituent Thr is similar to the amino acid Ser; the substituent Ser is similar to the amino acid Thr; the substituent Tyr is similar to the amino acid Trp; the substituents Ala and Pro are similar to the amino acid Gly; the substituents Asn and Gln are similar to the amino acid His; the substituents Leu and Val are similar to the amino acid Ile; the substituents Ile and Val are similar to the amino acid Leu; the substituents Arg, Gln and Glu are similar to the amino acid Lys; the substituents Leu, Tyr and Ile are similar to the amino acid Met; the substituents Met, Leu and Tyr are similar to the amino acid Phe; the substituents Trp and Phe are similar to the amino acid Tyr; and the substituents Ile and Leu are similar to the amino acid Val.

Such substantial changes can be achieved by substitutions with amino acids which are more different in their structures and functional groups. The effects of substantial changes are a significant change of the three-dimensional structure and/or, for example, an influence on the sheet structure or helical structure. Interactions between charges and hydrophobic chains are also to be observed in the changes.

Such analyses through substitutions can be easily accomplished. Thus, one amino acid in one position at a time is exchanged with, preferably, alanine or another amino acid. After the synthesis of the modified protein, the function of the altered protein is measured. The functions and their measurement are illustrated in the Examples. Multiple substitutions are also possible.

Definitions

The abbreviations used in the text are determined by rules which have been established by the IUPAC-IUB Commission for biochemical nomenclature (Bio-chemistry 11: 1726 (1972), and Biochem. J. 219: 345 (1984)). The following usual abbreviations are used: Ala=A=alanine; Arg=R=arginine; Asn=N= asparagine; Asp=D=aspartic acid; Cys=C=cysteine; Gln=Q=glutamine; Glu=E=glutamic acid; Gly=G=glycine; His=H=histidine; Ile=I=isoleucine; Leu=L=leucine; Lys=K=lysine; Met=M=methionine; Phe=F=phenylalanine; Pro=P=proline; Ser=S=serine; Thr=T=threonine; Trp=W=tryptophan; Tyr=Y=tyrosine; and Val=V=valine.

The protective group of residue $R_N$ can consist of:

Alkyl, aryl, alkylaryl, aralkyl, alkylcarbonyl or arylcarbonyl groups having from 1 to 10 carbon atoms, preferably naphthoyl, naphthylacetyl, naphthylpropionyl, benzoyl groups, or an acyl group having from 1 to 7 carbon atoms.

The protective group of residue $R_C$ can consist of:

An alkoxy or aryloxy group having from 1 to 10 carbon atoms, or an amino group.

Further protective groups, for both $R_N$ and $R_C$, are described in Houben-Weyl (1974), Georg Thieme Verlag, 4th Edition. The description of the protective groups in the stated literature is included herein by reference.

The sequences of the peptides or peptide derivatives according to the invention can be connected with further flanking amino acid sequences instead of a protective group on the N-terminal and/or C-terminal ends. These further flanking amino acid sequences are not essential to the function of the peptides or peptide derivatives according to the invention, but they may be carriers of other functions, for example, comprise enzymatic functions. Such flanking amino acid sequences are occurring in the nature. They may be, for example, the sequences of the variable region of an antibody which are positioned between the hypervariable regions. These sequences are referred to as framework sequences. Further known flanking amino acid sequences include uncleaved signal sequences of a secreted eukaryotic protein, the protein being expressed in a bacterium. Such signal sequences sometimes have no influence on the function of the subsequent protein. It is also possible to couple peptides or peptide derivatives according to the invention in succession, with flanking amino acid sequences being provided between the individual sequences. Also, fusion proteins are known in which the peptide is linked through a peptide bond on the N-terminal or C-terminal end. Such a fusion protein can be expressed by bacteria or eukaryotic cells.

In particular cases, in order to decide whether a particular peptide or peptide derivative according to the invention having at least one flanking amino acid sequence and/or at least one protective group belongs to the subject matter of the invention, a comparison is to be made between:

(i) this peptide or peptide derivative with the flanking amino acid sequence and/or with the protective group; and (ii) the same peptide or peptide derivative without the flanking amino acid sequence and without the protective group.

Both molecules should essentially have the same function as the peptides from the group of reference sequences, i.e., to induce the production of interferon-γ or TNF-α in $CD8^+$ T cells, especially from subjects immunized with HCMV and having the appropriate HLA type.

The stated amino acids are natural or artificial amino acids. The artificial amino acids are described in Houben-Weyl (1974), Georg Thieme Verlag, 4th Edition. The exchange of a described amino acid with another amino acid which belongs to the group of natural or artificial amino acids is easy to perform. Based on the test system and the comparison with one of the peptides from the group of reference sequences explicitly stated above, it is easy to find out whether an effect exists which is equal or similar to the effect of the found substances according to the invention. All D-amino acids and all amino acids which can be prepared synthetically (Houben-Weyl) also fall under the scope of protection. For the skilled person, it is easy to modify the molecular structure while retaining the essential components so that the functions which can be checked in the test are maintained. Such functionally equivalent molecules also fall under the concept of peptide derivatives.

Advantages

The peptides or peptide derivatives according to the invention allow to selectively produce vaccines against infection by human cytomegalovirus. The peptides and peptide derivatives may also be used as diagnostic agents for determining whether the subjects to be examined, especially those having the appropriate HLA type, possess CD8+ T cells which are induced by substances according to the invention to production of interferon-γ or TNF-α (tumor necrosis factor α).

Preferred Embodiments

Preferred sequences include nonamers formed by truncating a longer sequence as explicitly stated above or their derivatives to nine contiguous amino acids. The deletion may be an N-terminal and/or C-terminal deletion. It is essential that the functionality of a peptide from the group of reference sequences is essentially met. The reason why nonamers are very potent stimulants of CD8+ T cells is the fact that MHC class I presented peptides typically have a length of nine amino acids (K. O. Falk et al. (1991), Allele-specific motifs revealed by sequencing of self-peptides eluted from MHC molecules, Nature, Vol. 351, pp 290–296, and H. G. Rammensee et al. (1999), An Internet Database for MHC Ligands and Peptide Motifs, http://134.296.221/scripts/hlaserver.dll/home.htm).

It is also possible to link the above mentioned nonamers with further amino acids through peptide bonds to form sequences of at least 10 amino acids. These sequences also have the functionality to induce the production of interferon-γ or TNF-α in CD8+ T cells. Thus, the scope of protection of the invention also encompasses sequences extended by at least one amino acid of nonamers which have the functionality to induce the production of interferon-γ or TNF-α in CD8+ T cells, especially from subjects immunized with HCMV and having the appropriate HLA type. For the extended nonamers, it is essential also to have the functionality to induce the production of interferon-γ or TNF-α in CD8+ T cells, especially from subjects immunized with HCMV and having the appropriate HLA type.

Preparation of the Peptides

Further, the peptides or peptide derivatives according to the invention can be easily prepared. Such short peptides or peptide derivatives can be prepared using a technique which is known to those skilled in the art of peptide synthesis. A survey of many of these techniques can be looked up in J. M. Stewart and J. D. Young, San Francisco, 1969; and J. Meierhofer, Hormonal Proteins and Peptides, Vol. 2, p 46, Academic Press (New York), 1973, for the solid-phase method, and E. Schroder and K. Lubke, The Peptides, Vol. 1, Academic Press (New York), 1965, for the liquid-phase method. The steps of the synthesis are described in EP-A 0 097 031. The general process steps from the European publications can be transferred by analogy to the synthesis of the peptides or peptide derivatives according to the invention as herein described. Further references relating to solid-phase synthesis include: Solid Phase Synthesis, E. Atherton and R. C. Sheppard (1989), IRL Press, ISBN 1-85221-133-4, and Amino Acid and Peptide Synthesis, J. Jones, Oxford Science Publication (1992), ISBN 0-19-855668-3.

Further Embodiments in Terms of the Residues

In addition to modification of the amino acid sequence of the peptides or peptide derivatives according to the invention, it is also possible to vary the residues $R_N$ and $R_C$. However, the residues need not influence the function. Nevertheless, parameters such as stability, pH dependence, biodegradability and interactions with the native part of the fusion protein can be significantly affected by protective groups.

Preferred are peptides or peptide derivatives according to the invention in which residue
$R_N$ represents —H or an amino protective group; and
$R_C$ represents —OH or a carboxy protective group.
More preferred are peptides or peptide derivatives according to the invention in which residue
$R_N$ represents —H or an acyl group; and
$R_C$ represents —OH or an amino group.
Most preferred are peptides or peptide derivatives according to the invention in which residue
$R_N$ represents —H; and
$R_C$ represents —OH.

Preparation Methods for the Peptides According to the Invention

The invention further comprises the preparation of the peptides or peptide derivatives according to the invention, wherein an N-α-protected ω-amino-α-amino acid is reacted with a dialdehyde in the presence of a reductant, followed by deprotecting the side chains and optionally deprotecting the N-terminus and/or the C-terminus.

The invention also relates to a process in which the peptides or peptide derivatives according to the invention are prepared by condensing the amino acids in a homogeneous phase or by the solid-phase method;
wherein the carboxy end of an amino acid to be coupled whose amino groups and optionally side chain functional groups bear a protective group reacts with the free amino end of the amino acid to be coupled or the peptide to be coupled in the presence of a condensation reagent; and
in the case of a non-terminal amino acid, the α-amino protective group of the coupled amino acid is subsequently cleaved off, and other amino acids are coupled to the peptide chain to be synthesized according to the two steps described above; or
in the case of a non-terminal amino acid, optionally, the α-amino protective group of the coupled amino acid is subsequently cleaved off; and
in the case of the solid-phase method, after the coupling of the last amino acid, the peptide or peptide derivative is cleaved from the solid phase.

Use as a Medicament

The peptides or peptide derivatives according to the invention are suitable for use as a medicament or diagnostic agent.

Most preferred is the use of a peptide or peptide derivative for preparing a medicament for vaccination against the human cytomegalovirus.

It is also advantageous to use a peptide or peptide derivative according to the invention for preparing a diagnostic agent for identifying a cellular immune response against HCMV. Thus, T cells of the patient can be stimulated in vitro with the peptides and peptide derivatives according to the invention. If this is accompanied by induction of the production of interferon-γ or TNF-α in CD8+ T cells, an immune response against HCMV has been detected. If such stimulation does not result in the induction of interferon-γ or TNF-α in CD8+ T cells of a subject immunized with HCMV and having the appropriate HLA type, this may mean that this subject has not built a CD8+ T cell response against the HCMV, or an existing CD8+ T cell response is not directed against the epitope used for stimulation.

It is particularly advantageous to use a peptide or peptide derivative according to the invention for preparing a diagnostic agent for identifying an immune response against HCMV in immunodeficient subjects.

The immune response against HCMV identified through the induction of INF-γ or TNF-α in CD8+ T cells can be quantified by determining the number of CD8+ T cells in which induction of these cytokines has occurred. This number can be stated as an absolute (per volume of the starting material) or relative value (for example, based on all CD8+ T cells). Such quantification can be effected, for example, by flow cytometry or by another suitable method.

As a medicament, it is preferred for the peptides or peptide derivatives according to the invention to form a composition with pharmacologically acceptable auxiliary agents and carriers. Such auxiliary agents and carriers are described in Remington's Pharmaceutical Science, 15th Ed., Mack Publishing Company, East Pennsylvania (1980). The compositions can be prepared by known methods.

It is advantageous to use the peptides or peptide derivatives for loading dendritic cells, which are subsequently administered to a patient as a medicament. It is more advantageous to use the peptides or peptide derivatives for loading HLA-identical or partially HLA-identical dendritic cells which are subsequently administered to a patient as a medicament.

The use of peptide-loaded dendritic cells as a vaccine is described in Brugger et al., Ann. N.Y. Acad. Sci., Vol. 872, pp 363–371.

The peptides or peptide derivatives according to the invention have pharmacological properties and can therefore be used as a pharmaceutically active substance or diagnostic agent, especially as a vaccine or diagnostic agent. The invention also relates to a medicament which contains the peptides or peptide derivatives according to the invention.

The experimental results of the in-vitro testing show that the peptides or peptide derivatives according to the invention can be used as medicaments or for medical treatment. These experimental results can be transferred without any problem from the in-vitro test system to an in-vivo system.

The invention further provides
(i) the use of peptides or peptide derivatives according to the invention (for preparing a medicament) as vaccines against infections with HCMV;
(ii) a pharmacological composition as a vaccine against infections with HCMV which, for treatment or prophylaxis, comprises the peptides or peptide derivatives according to the invention and at least one pharmaceutically acceptable auxiliary agent and/or carrier.

Different doses are suitable for providing a therapeutic effect. They depend, for example, on the salts employed, on the host, on the kind of administration and on the type and severity of the conditions to be treated.

Combinations of the peptides or peptide derivatives according to the invention are also possible.

The invention further relates to DNA (deoxyribonucleic acid) which codes for one of the above mentioned amino acid sequences and their derivatives.

Such DNA can be usefully incorporated in vectors or plasmids. Such vectors are capable of intruding into human cells and start protein biosynthesis therein. In this form, the protein biosynthetic apparatus of the human can be used for synthesizing and secreting the desired peptides.

With differently coding DNA, such vectors are described in D. Salmon-Ceron et al. (1999), AIDS Res. Hum. Retroviruses, Vol. 15/7, pp 633–645, and F. Dorner et al. (1999), Ann. Med. Vol. 31/1, pp 51–60, and G. Ferrari et al. (1997), Blood, Vol. 90, pp 2406–2416, and K. Molling (1998), Z. Ärztl. Fortbild. Qualitätssich., Vol. 92, pp 681–683, and M. Giese (1998), Virus Genes, Vol. 17, pp 219–232.

EXAMPLES

Methods

Citrated blood was obtained from anti-HCMV-IgG-seropositive blood donors of a defined HLA type. A Ficoll-Paque density centrifugation was performed. The cells were washed with sterile PBS and resuspended in RPMI 1640 which contained 0.10% BSA and 2 mM glutamine. The cells were adjusted to $10^7$ cells per ml. Two hundred microliters of the cell suspension and of the peptide solution (10 μg per ml in RPMI/BSA) was filled into Cellstar® polystyrene tubes and stored in an incubator.

After one hour, 1600 μl of RPMI 1640 which contained 12.50% FCS, 50 mM glutamine and 12.5 μg per ml of brefeldin A was added. After another five hours, the cells were washed with cold PBS, resuspended in PBS with 1 mM EDTA, incubated at 37° C. for another 10 minutes, and again washed with cold PBS.

After surface labeling with monoclonal antibodies for 30 minutes at 4° C. in the dark, the cells were fixed in PBS containing 40% paraformaldehyde for 4 minutes at 37° C., followed by washing with PBS. The cells were then permeabilized using the permeabilization solution of Becton Dickinson (Heidelberg), followed by another wash with PBS.

Subsequent to the following intracellular labeling with monoclonal antibodies against interferon-γ and/or TNF-α, the cells were again washed in PBS and analyzed with a FACScalibur® flow cytometer (Becton Dickinson) using CellQuest™ software. Unstimulated samples were employed as controls.

Results

The substances according to the invention exhibited a stimulation of the CD8+ T cells. Therefore, these substances are suitable as vaccines. Further, they are suitable for use as diagnostic agents, wherein the cells which can respond to HCMV are identified. The inability or ability of a patient to respond to HCMV or an immunization with HMCV which has already taken place are established by this form of diagnose. The stimulation of the CD8+ T cells was detected by the presence of intracellularly retained interferon-γ or tumor necrosis factor α (TNF-α).

Preparation of the Peptides

The synthesis of peptides or peptide derivatives can be performed on a Multiple Peptide Synthesizer (MPS) AMS 422 of ABIMED (Langenfeld) (H. Gausepohl et al. (1992), Peptide Research 5/6: 315–320).

As solid supports for the peptide synthesis, hardened cellulose (Whatman 540; Catalogue No. 1540917) of Whatman (Maidstone, Great Britain) and polystyrene resin Tenta Gel SRAM (capacity 0.25 meq/g) of Rapp Polymere (Tübingen, Germany) can be used.

The solid-phase peptide synthesis is described extensively in Rudolf Volkmer-Engert, Berit Hoffmann, and lens Schneider-Mergener (1997), Stable Attachment of the HMB-Linker to Continuous Cellulose Membranes for Parallel Solid Phase Spot Syntheses, Tetrahedron Letter, Vol. 38,6; pp 1029–1032.

The invention claimed is:

1. An isolated or purified peptide selected from the group consisting of:
- $R_N$-Ala Arg Ala Lys Lys Asp Glu Leu Arg Arg Lys Met Met Tyr Met-$R_C$ (SEQ ID No. 2),
- $R_N$-Asp Glu Leu Arg Arg Lys Met Met Tyr Met-$R_C$ (SEQ ID No. 3)
- $R_N$-Glu Leu Arg Arg Lys Met Met Tyr Met-$R_C$ (SEQ ID No. 9)
- $R_N$-Asp Glu Leu Arg Arg Lys Met Met Tyr-$R_C$ (SEQ ID No. 10), and
- derivatives of $R_N$-Ala Arg Ala Lys Lys Asp Glu Leu Arg Arg Lys Met Met Tyr Met-$R_C$ (SEQ ID No. 2) having a substitution of one, two or three amino acids; wherein $R_N$ represents —H or an amino protective group, $R_C$ represents —OH or a carboxy protective group, and said peptide has the ability to induce the production of interferon-γ or TNF-α in CD8$^+$ T cells.

2. The peptide according to claim 1 having the sequence
- $R_N$-Ala Arg Ala Lys Lys Asp Glu Leu Arg Arg Lys Met Met Tyr Met-$R_C$ (SEQ ID No. 2),
- $R_N$-Asp Glu Leu Arg Arg Lys Met Met Tyr Met-$R_C$ (SEQ ID No. 3),
- $R_N$-Glu Leu Arg Arg Lys Met Met Tyr Met-$R_C$ (SEQ ID No. 9), or
- $R_N$-Asp Glu Leu Arg Arg Lys Met Met Tyr-$R_C$ (SEQ ID No. 10).

3. The peptide according to claim 1, wherein $R_N$ represents —H or an acyl group and $R_C$ represents —OH or an amino group.

4. The peptide according to claim 3, wherein $R_N$ represents —H and $R_C$ represents —OH.

5. Method for identifying a cellular immune system response against HCMV, said method comprising:
   a) incubating T-cells with a peptide according to claim 1; and
   b) detecting whether incubation has resulted in the production of interferon-γ or TNF-α in CD8$^+$ T cells, wherein production of interferon-γ or TNF-α in the CD8$^+$ T cells identifies a cellular immune system response against HCMV.

6. Method for quantifying a response of the cellular immune system against HCMV, said method comprising:
   a) incubating T-cells with a peptide according to claim 1; and
   b) detecting the number of CD8$^+$ T cells that have been induced to produce interferon-γ or TNF-α, wherein the number of induced CD8$^+$ T cells quantifies a cellular immune system response against HCMV.

7. An isolated or purified DNA which codes for a peptide according to claim 1.

8. A plasmid or vector comprising a DNA according to claim 7.

* * * * *